(12) United States Patent
Kan

(10) Patent No.: US 6,894,495 B2
(45) Date of Patent: May 17, 2005

(54) AIR FEED DEVICE, SIGNAL ACQUISITION DEVICE AND IMAGING DEVICE

(75) Inventor: Koji Kan, Tokyo (JP)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 130 days.

(21) Appl. No.: 09/914,631

(22) PCT Filed: Feb. 1, 2001

(86) PCT No.: PCT/US01/03311

§ 371 (c)(1),
(2), (4) Date: Aug. 30, 2001

(87) PCT Pub. No.: WO01/56493

PCT Pub. Date: Aug. 9, 2001

(65) Prior Publication Data

US 2002/0135370 A1 Sep. 26, 2002

(30) Foreign Application Priority Data

Feb. 4, 2000 (JP) ......................................... 2000-27652

(51) Int. Cl.$^7$ ................................................ G01V 3/00
(52) U.S. Cl. ...................................... 324/318; 324/315
(58) Field of Search ................................. 324/300–322; 700/273; 60/420; 600/529, 104, 109; 62/243

(56) References Cited

U.S. PATENT DOCUMENTS

| | | | | |
|---|---|---|---|---|
| 3,983,715 A | * | 10/1976 | Hair, Jr. et al. ................ | 62/243 |
| 4,179,888 A | * | 12/1979 | Goscenski, Jr. ............... | 60/420 |
| 4,859,948 A | * | 8/1989 | Kuster ......................... | 324/318 |
| 4,960,106 A | * | 10/1990 | Kubokawa et al. .......... | 600/104 |
| 5,035,231 A | * | 7/1991 | Kubokawa et al. .......... | 600/109 |
| 5,335,651 A | * | 8/1994 | Foster et al. ............ | 128/202.13 |
| 5,337,845 A | * | 8/1994 | Foster et al. .................. | 180/11 |
| 5,457,831 A | * | 10/1995 | Foster et al. .................... | 5/510 |
| 5,485,850 A | * | 1/1996 | Dietz ........................... | 600/529 |
| 5,497,766 A | * | 3/1996 | Foster et al. ............ | 128/200.24 |
| 5,497,776 A | * | 3/1996 | Yamazaki et al. ........... | 600/445 |
| 5,602,477 A | * | 2/1997 | McCarthy et al. ........... | 324/315 |
| 5,946,220 A | * | 8/1999 | Lemelson ................... | 700/273 |
| 2002/0135370 A1 | * | 9/2002 | Kan ............................ | 324/318 |

FOREIGN PATENT DOCUMENTS

| DE | 3528821 |  | 2/1987 | |
|---|---|---|---|---|
| DE | 3528821 A1 | * | 2/1987 | ............ F01P/07/04 |

* cited by examiner

Primary Examiner—Christopher W. Fulton
Assistant Examiner—Tiffany A. Fetzner
(74) Attorney, Agent, or Firm—Jay L. Chaskin; CantorColburn LLP

(57) ABSTRACT

An air feed device comprises a fluid motor to drive rotating vanes and blow air with high efficiency into a space accommodating a subject in a magnetic resonance device. The air feed device does not cause electrical interference with the magnetic imaging device.

16 Claims, 16 Drawing Sheets

AIR FEED DEVICE, SIGNAL ACQUISITION DEVICE AND IMAGING DEVICE

This is a application of International Application No. PCT/US01/03311 filed Feb. 1, 2001.

BACKGROUND OF THE INVENTION

The present invention relates to means for feeding air, means for signal acquisition, and a means for imaging, and relates in particular to means for feeding an air blow to or into a space for storing the subject for measurement, means for signal acquisition, and means for imaging comprised of such a means for feeding air.

In a magnetic resonance imaging device, the subject for imaging is positioned into an inner space of the magnet system, or in other words into an image capture space formed of a static magnetic field. A gradient magnetic field and a high frequency magnetic field are applied to generate a magnetic resonance signal within the imaging subject, and a cross sectional image is generated (reconstructed) based on that received signal.

An air blow (or breeze) is fed into the image capture space to provide a cool feeling to the subject for imaging. The air or breeze is blown to or into the image capture space from an air duct by an electric air blower installed at a location well separated from image capture space, so that the electric air blower does not electrically interfere with the magnetic resonance signal.

The above air feed device had poor efficiency because of energy losses in the air duct.

BRIEF DESCRIPTION OF THE INVENTION

An embodiment of the present invention provides a means for air feed of high efficiency, means for signal acquisition comprised of such means for air feed, and means for imaging.

A first embodiment of the invention comprises of a fluid motor rotatably driven by the flow of fluid, and a rotating vane to force air into a space holding the subject for imaging.

In this first embodiment of the invention, rotating vanes generate an air blow (or breeze) by utilizing a fluid motor as a motive source. The fluid motor does not generate electrical interference signals and so can bring about an air blow (or breeze) near the imaging subject, and can blow the air with high efficiency.

A second embodiment of the invention comprises means for signal acquisition having a space to store the signal acquisition object, a fluid motor rotatably driven by the flow of fluid, a rotating vane driven by the fluid motor to generate an air blow in the space, and a rotation transmission means to transmit the rotation of the vanes.

In the second embodiment of the invention, the rotating vanes generate a breeze utilizing the fluid motor as a motive source. The fluid motor does not generate electrical interference signals and can therefore generate a breeze near the signal acquisition subject, and blow the air with high efficiency.

A third embodiment of the invention comprises means for signal acquisition according to the second embodiment of the invention includes a signal acquisition means having a section to be cooled by the fluid, and the fluid motor is driven by fluid to cool the section to be cooled.

In this third embodiment of the invention, the fluid for cooling in the means for signal acquisition rotates the fluid motor so that a simple structure combining the cooling system and fluid motor drive system can be achieved.

A fourth embodiment of the invention comprises means for imaging wherein the means for imaging has a space to store the imaging subject, a fluid motor rotatably driven by the flow of fluid, and rotating vanes driven by the motor to force air into the space storing the imaging subject.

In this fourth embodiment of the invention, the rotating vanes generate a breeze utilizing the fluid motor as a motive source. The fluid motor does not generate electrical interference signals and can therefore generate a breeze near the signal acquisition subject, and blow the air with high efficiency.

A fifth embodiment of the invention comprises means for imaging according to the fourth embodiment of the invention and includes means for signal acquisition having a section to be cooled by the fluid, and the fluid motor is driven by fluid to cool the section to be cooled.

In this fifth embodiment of the invention, the fluid for cooling in the imaging means rotates the fluid motor so that a simple structure combining the cooling system and fluid motor drive system can be achieved.

Therefore, the embodiments of the invention provide a highly efficient air feed device, as well as a means for signal acquisition and a means for imaging comprising the means for air feed.

The present invention will be apparent from the following description of the preferred embodiments of the invention as illustrated in the accompanying drawings in which.

DETAILED DESCRIPTION OF THE INVENTION

Figure 1:
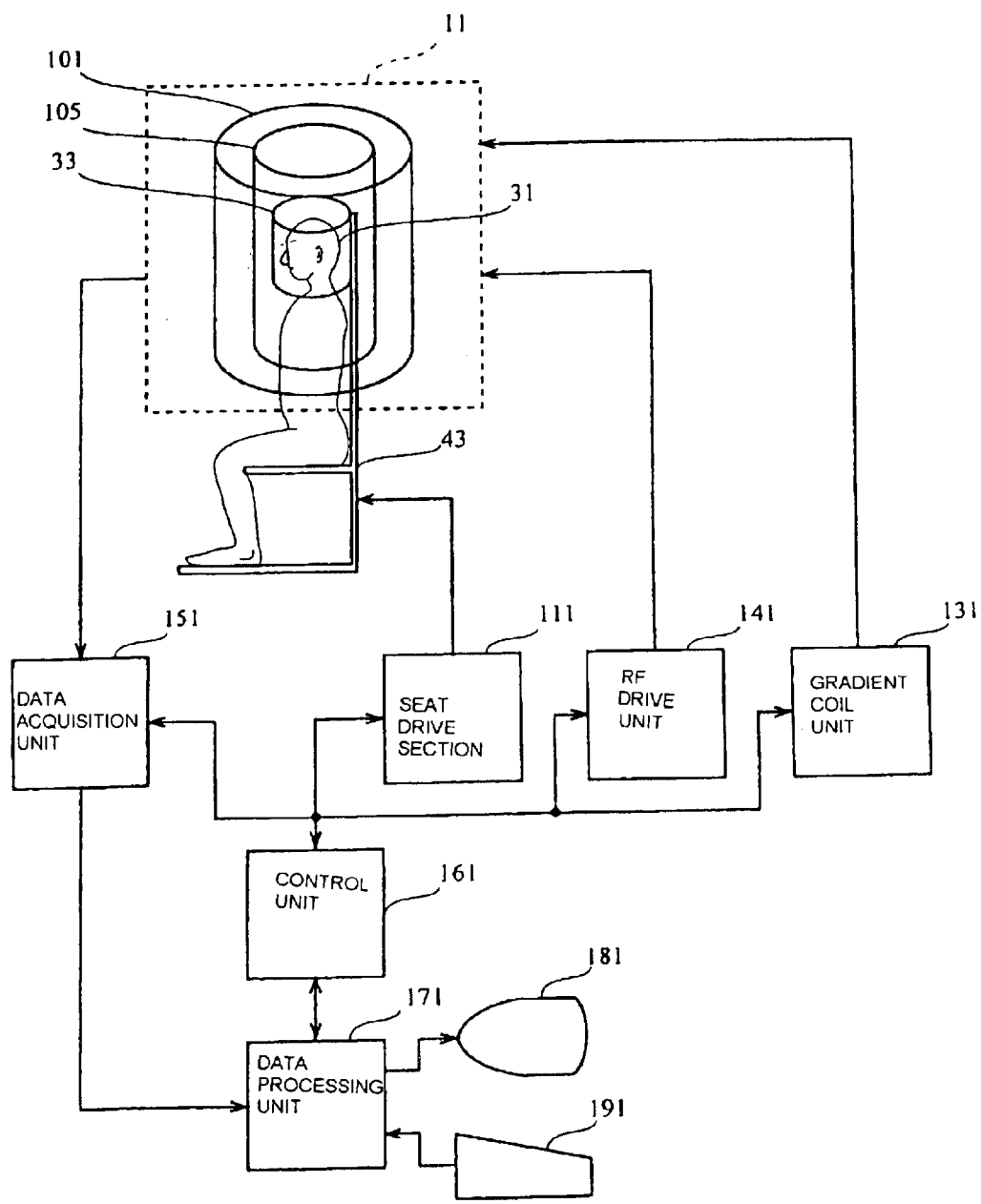
FIG. 1 is a block diagram showing a magnetic resonance imaging system.

A block diagram of the magnetic resonance imaging system is shown in FIG. 1. This system is an embodiment of the invention. An example of the embodiment of the invention is shown by means of the structure of this system.

The system as shown in FIG. 1 has a magnet system 11. The magnet system 11 has a main magnetic field coil unit 101 and a gradient coil unit 105. Each of these coils has a generally cylindrical shape and are arranged mutually concentric to each other. The bore of the magnet system 11 faces perpendicularly and so this system is called a vertical bore magnet system.

Though not shown in the drawing, the magnet system 11 is comprised of an air blow device to supply a breeze (air blow) to an internal space. This air feed device is described again later on.

A subject to be imaged 31 is seated on a seat 43 and carried in to the generally columnar inner space of the magnet system 11. The center axis of the generally columnar inner space faces perpendicularly. The shape of the internal space is not limited to a columnar shape but may also be a pillar shaped inner space having a lateral cross section of an appropriate shape. The subject 31 takes an upright posture by sitting in the sear 43. The seat 43 occupied by the subject 31 is driven to advance and retract vertically by a seat drive section 111.

The head of the subject 31 is held inside the RF (radio frequency) coil 33 installed above the back of the seat 43. The RF coil 33 is comprised for example, of a TEM (transverse electromagnetic mode) resonator type RF coil. The RF coil 33 also has a generally cylindrical shape and is installed in the inner space of the magnet system 11 along the same axis as the main magnetic field coil unit 101 and a gradient coil unit 105.

The main magnetic field coil unit 101 forms a static magnetic field in the inner space (bore) of the magnet system 11. The main magnetic field coil unit 101 is formed by utilizing for example, a super-conductive coil. Of course, this invention is not limited to use of a super-conductive coil and may use an ordinary conductive coil.

The gradient coil unit 105 generates a gradient magnetic field for making the static magnetic field intensity have a gradient. The generated gradient magnetic field is of three types: a slice gradient field, a readout gradient field and a phase encode gradient magnetic field. The gradient coil unit 105 has a three-system gradient coil (not shown in the drawing) for these three types of gradient magnetic fields.

The RF coil 33 configures a high frequency magnetic field for excitation a spin within the body of the subject 31 in the static magnetic field space. The forming of the high frequency magnetic field is referred to as transmission of the RF excitation signal. The transmission of the RF excitation signal may also be performed by a dedicated transmission RF coil separate from the RF coil 33. The RF coil 33 receives the magnetic waves generated by the excited spin or in other words the magnetic resonance signal.

The gradient coil unit 131 applies a drive signal to the gradient coil unit 105 and generates a gradient magnetic field. The gradient drive unit 131 has three system drive circuits not shown in the drawing, corresponding to the three types of gradient coils in the gradient coil unit 105. The RF drive unit 141 applies a drive signal to the RF coil unit 33, transmits an RF excitation signal, and causes spin excitation within the body of the subject 31. The data acquisition unit 151 is input with the receive signal received by the RF coil unit 33, and collects these signals as digital data.

The seat drive section 111, gradient coil unit 131, RF drive unit 141 and the data acquisition unit 151 are controlled by the control unit 161. The section constituted by the magnet system 11, seat drive section 111, gradient coil unit 131, RF drive unit 141, data acquisition unit 151 and the control unit 161 are typical elements in an embodiment of the means for signal acquisition.

The data processing unit 171 is input with signals output from the data acquisition unit 151. The data processing unit 171 stores data input from the data acquisition unit 151 into the memory not shown in the drawing.

The memory is internally comprised of data spaces. These data spaces are comprised of two-dimensional Fourier spaces. The data processing unit 171 performs two-dimensional inverse Fourier conversion of these two-dimensional Fourier spatial data and generates (reconstructs) a sectional layered image of the head of the subject 131.

The data processing unit 171 coordinates the processing in the control unit 161. The display unit 181 displays the reconstructed image output from the data processing unit 171 and information of various types. The operating unit 191 inputs commands and information of various types to the data processing unit 171 by user operation.

The section constituted by the magnet system 11, seat drive section 111, gradient coil unit 131, RF drive unit 141, data acquisition unit 151 control unit 161, data processing unit 171, display unit 181 and the operating unit 191 are typical elements in an embodiment of the means for imaging.

Figure 2:
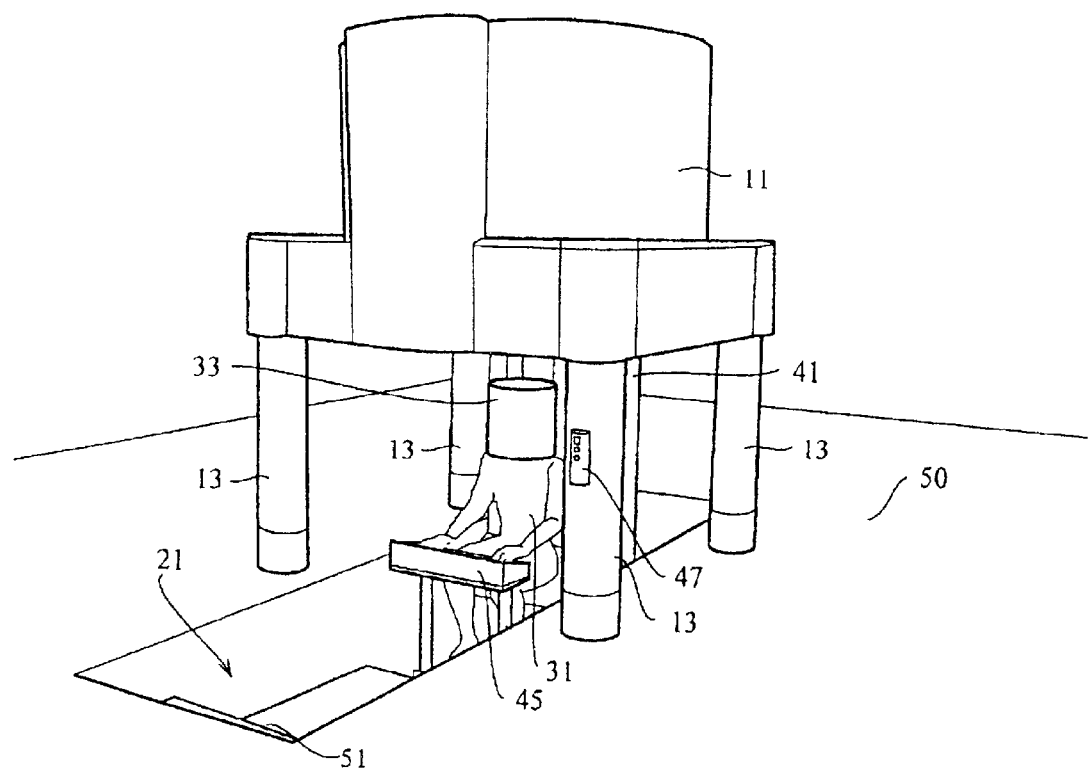
FIG. 2 is a perspective view of the external appearance of the magnet system of the system shown in FIG. 1 along with the imaging subject in standby state.
Figure 3:
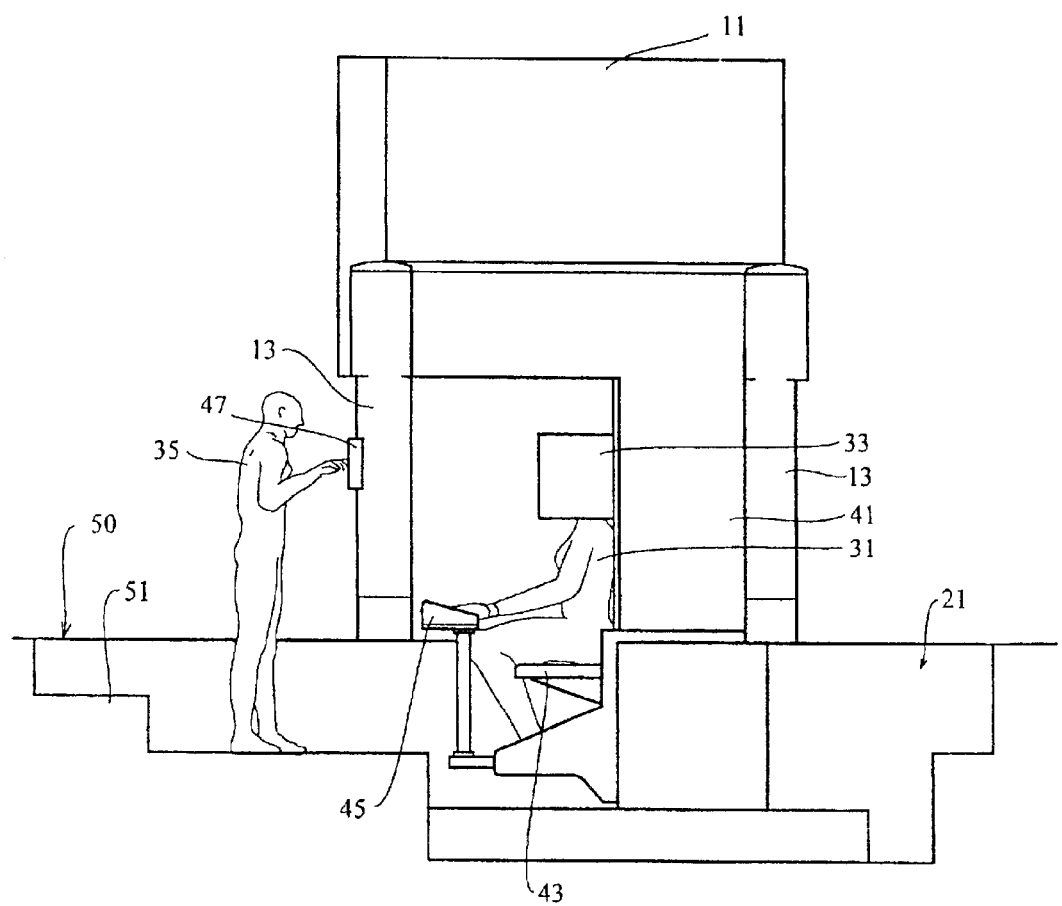
FIG. 3 is a side view of the external appearance of the magnet system shown in FIG. 1 along with imaging subject in standby state and the operator.

FIG. 2 and FIG. 3 show an external view of the subject 31 waiting in the magnet system 11. FIG. 2 is a perspective view and FIG. 3 is a side view showing a portion in cross section. As shown in these same figures, the magnet system 11 is supported by four support pillars 13 installed on the floor surface 50.

A pit 21 is made in the floor surface 50 below the magnet system 11. A stairs 51 are installed from the floor surface 50 downwards inside the pit 21. The seat 43 for seating the subject 31 is lowered by a seat up/down mechanism 41 to the bottom of the pit 21. The seat 43 and seat up/down mechanism 41 are made of nonmagnetic material.

A keyboard 45 such as for musical instruments is installed in front of the subject 31. The keyboard 45 is operated by the subject 31 during the imaging. The keyboard 45 is integrated into the seat. The keyboard operated by the subject 31 is not limited to a keyboard such as for musical instruments and may be a keyboard for information processors, or may be all types of equipment operated by hand such as tools, writing instruments or operating tools according to the subject of the test. Alternatively, equipment operated by the feed may be utilized according to the subject of the test.

One of the support pillars 13 is installed with an up/down switch 47. The up/down switch 47 forms a portion of the operating unit 191. Commands from the up/down switch 47 are applied to the seat drive section 111 by way of the control unit 161 and the data processing unit 171. The up/down switch 47 signal may also be directly applied to the seat drive section 111.

Figure 4:
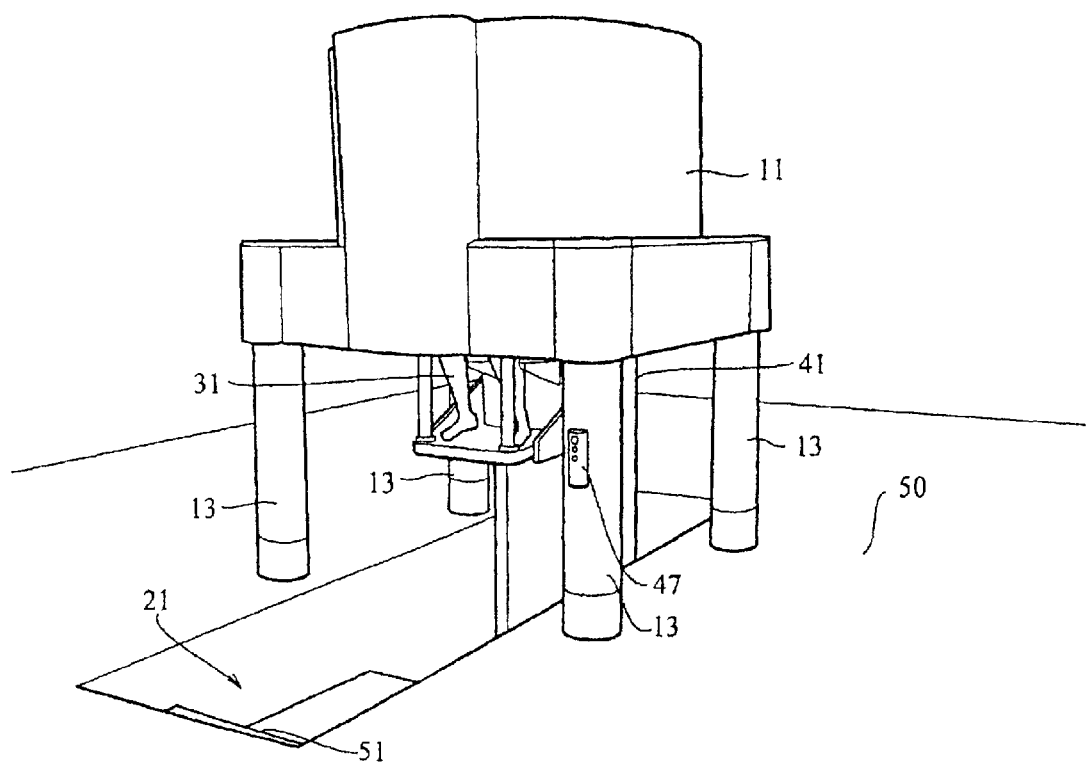
FIG. 4 is a perspective view of the external appearance of the magnet system shown in FIG. 1 along with imaging subject during the imaging operation.

The seat drive section 111 raises and lower the seat 43 by means of the seat up/down mechanism 41 according to the commands that were input. In other words, the seat 43 is raised during imaging as shown in FIG. 4, and the subject 31 is carried along with the RF coil 33 into the imaging space and when the imaging is finished, the seat 43 is lowered to a standby (waiting) position as shown in FIG. 1 and FIG. 2.

Figure 5:
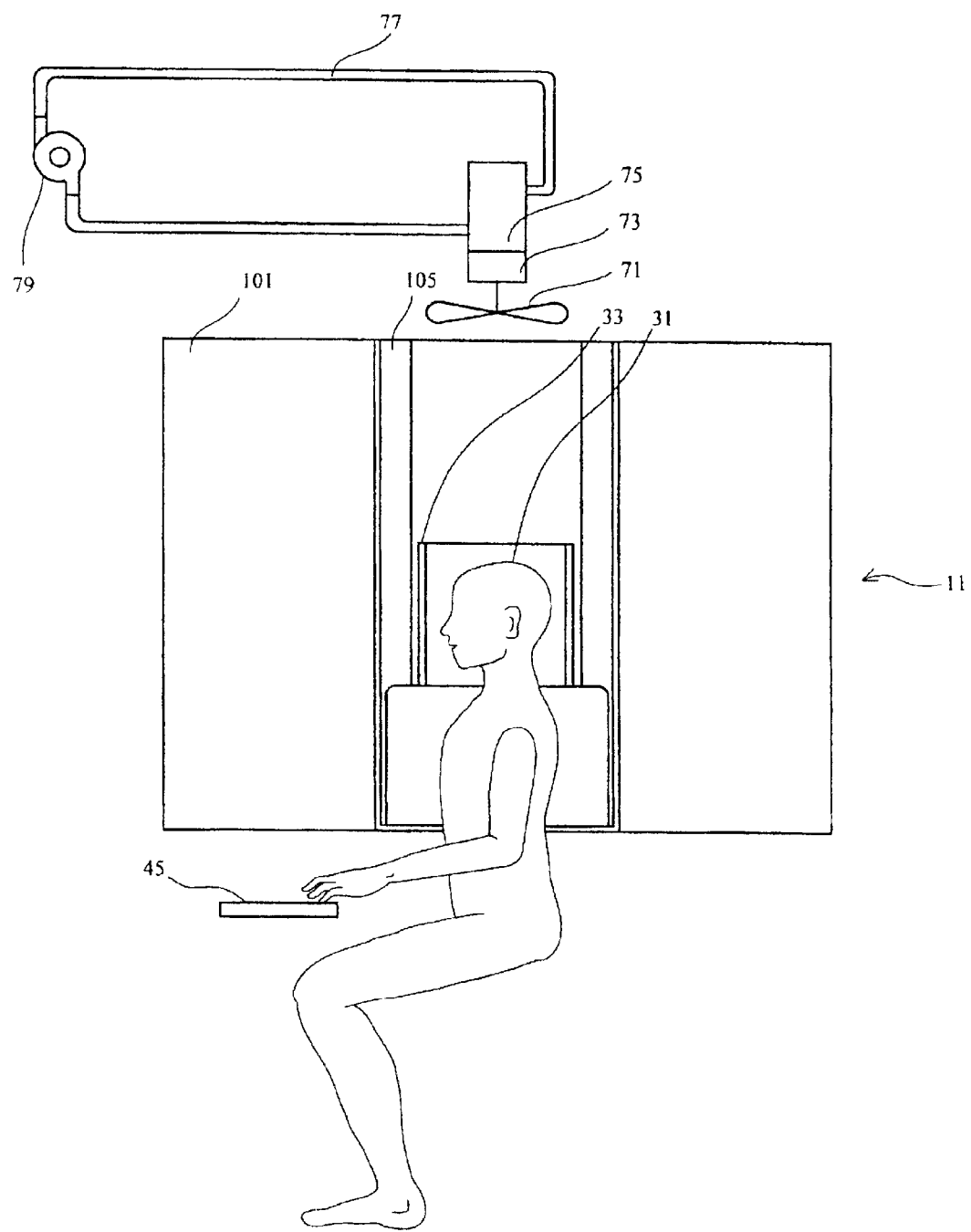
FIG. 5 shows an embodiment of the interrelation of the magnet system, the means for air feed and the imaging subject during the imaging operation.

The interrelation of the magnet system 11 and subject 31 and the RF coil 33 during imaging are shown in FIG. 5 along with the means for air feed. The head of the subject 31 and the RF coil 33 as shown in the same figure, are positioned in the center of the magnet system 11 or in other words, the magnet center of the imaging range.

The rotating vanes 71 are installed facing the bore in the upper part of the magnet system 11. The rotating vanes 71 may for example have a structure the same as the rotating vanes of a blower fan, and rotate to send air (breeze) into the inner space of the magnet system 11. The rotating vanes 71 are an example of an embodiment of the rotating vanes of the invention.

A rotating force is applied to the rotating vanes 71 from the fluid motor 75 by way of a gear box 73. The fluid motor 75 has a rotator element or in other words, a water wheel (not shown in drawing) in the interior of the casing, and the water wheel rotates by being driven by fluid such as oil or water circulating by way of the piping 77. The circulation of the fluid is performed by a pump 79 installed at a position adequately separated from the magnet system 11.

The rotation of the water wheel is conveyed to the rotating vanes 71 by way of the gear box 73. The gears within the gear box 73 can be shifted to allow adjustment of the rotational speed of the rotating vanes 71. An internal clutch is provided for turning the gears on and off allows intermittent conveyance of the motive force from the fluid motor 75 to the rotating vanes 71.

The control unit 161 controls the shifting of gears and turning of a clutch on and off. Needless to say, this control may be performed manually. The gear box 73 may be omitted when there is no need to adjust the rotational speed of the rotating vanes 71.

The rotating vanes 71, the gear box 73 and the fluid motor 75 are made of a nonmetallic material such as ceramic or plastic. The piping 77 may also be made of a nonmetallic material. The piping 77 may also be made of rubber.

The fluid motor 75, that comprises a means for air flow, uses no electricity and no magnetic signals are generated which may interfere with the magnetic resonance signal. Also, the gear box 73, the fluid motor 75 and the rotating vanes 71 are each made of a nonmetallic and nonmagnetic material such as plastic or ceramics so that the operation of these components does not disturb the electrical environment of the magnet system 11.

These components can be installed very near to the bore (inner space) entrance of the magnet system 11. Alternatively these components can also be installed in the inner space of the magnet system 11 if required. An installation of this type allows sending air with no losses or in other words sending an air blow (breeze) with high efficiency.

Figure 6:
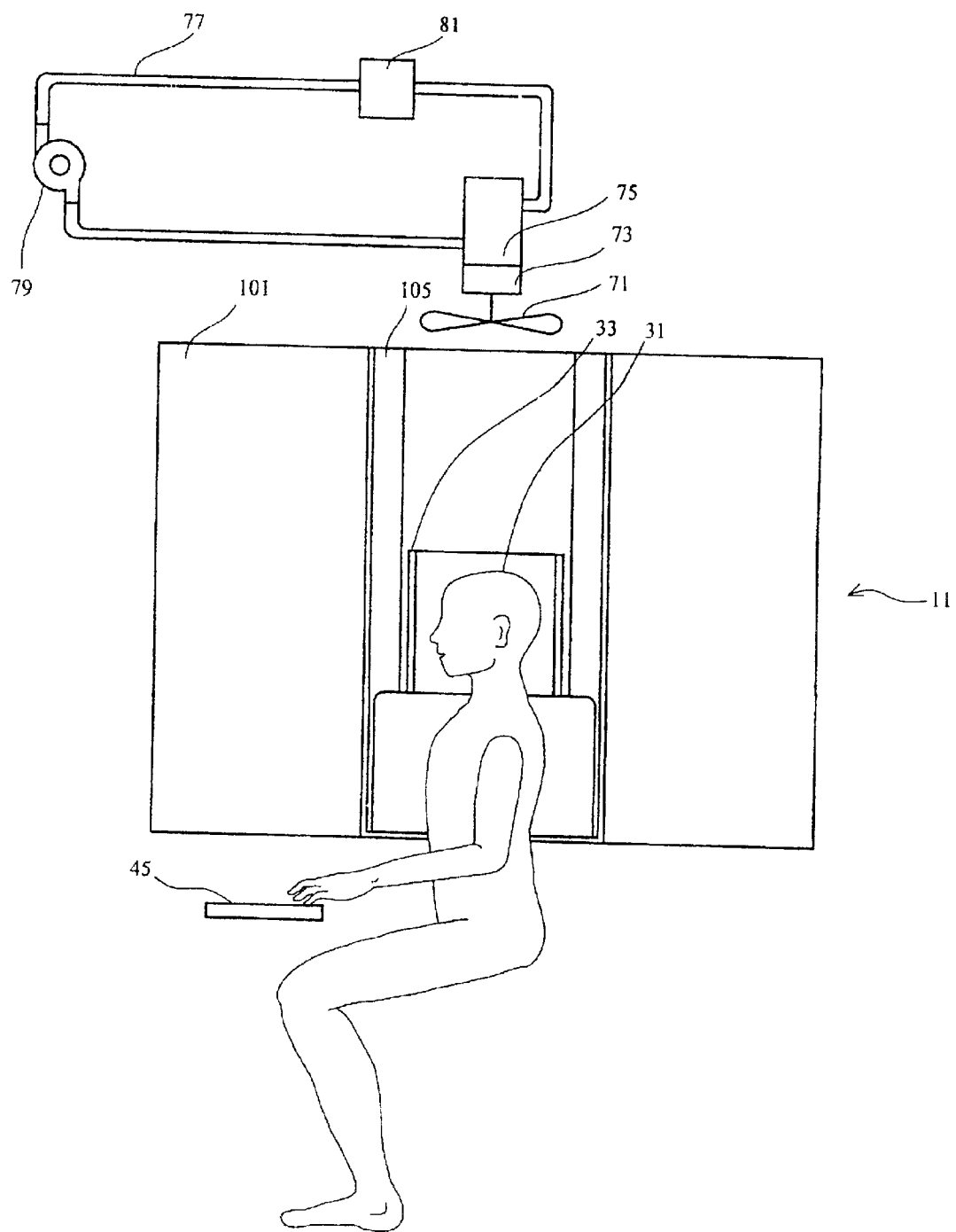
FIG. 6 shows an embodiment of the interrelation of the magnet system, the means for air feed, and the imaging subject during the imaging operation.

Adjustment of the rotational speed of the rotating vane 71 may also be made to adjust the flow rate of the fluid in the control valve 81 installed in the piping 77 as shown in FIG. 6. The flow rate adjuster valve 81 is an example of the embodiment of the means for adjustment. The flow rate adjuster valve 81 is also made of antimagnetic and nonmetallic material however this may not be required if installed a sufficient distance away from the magnet system 11.

The air flow rate adjustment by the flow rate adjuster valve 81 is performed automatically by the control unit 161 or manually adjusted by the operator. Alternatively, the air flow may also be adjusted by manually or automatically controlling the rotational speed of the pump 79 without using the flow rate adjuster valve 81. Further, needless to say, a joint adjustment by the flow rate adjuster valve 81 and adjustment of the pump 79 may also be employed.

Figure 7:
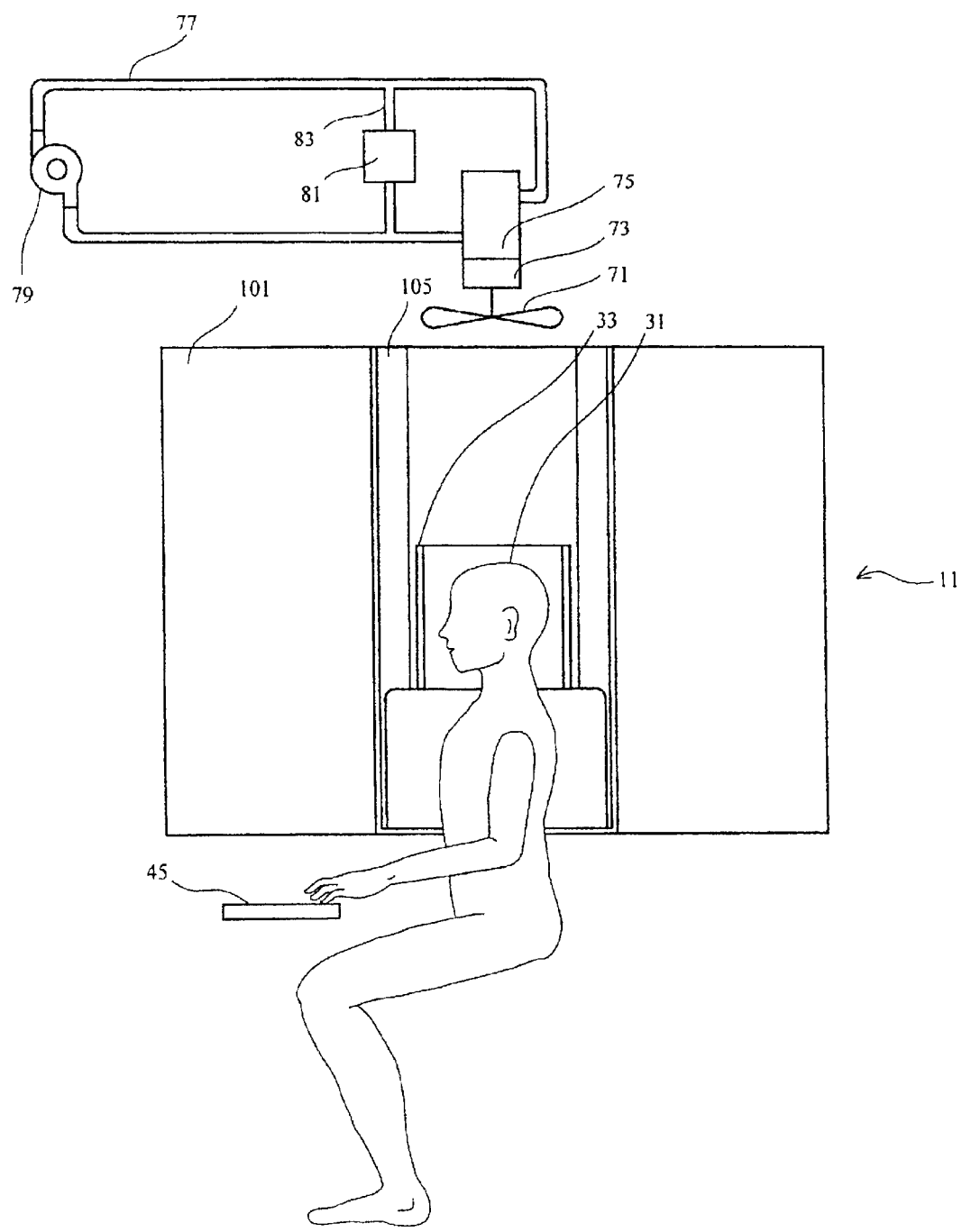
FIG. 7 shows an embodiment of the interrelation of the magnet system, the means for air feed, and the imaging subject during the imaging operation.
Figure 8:
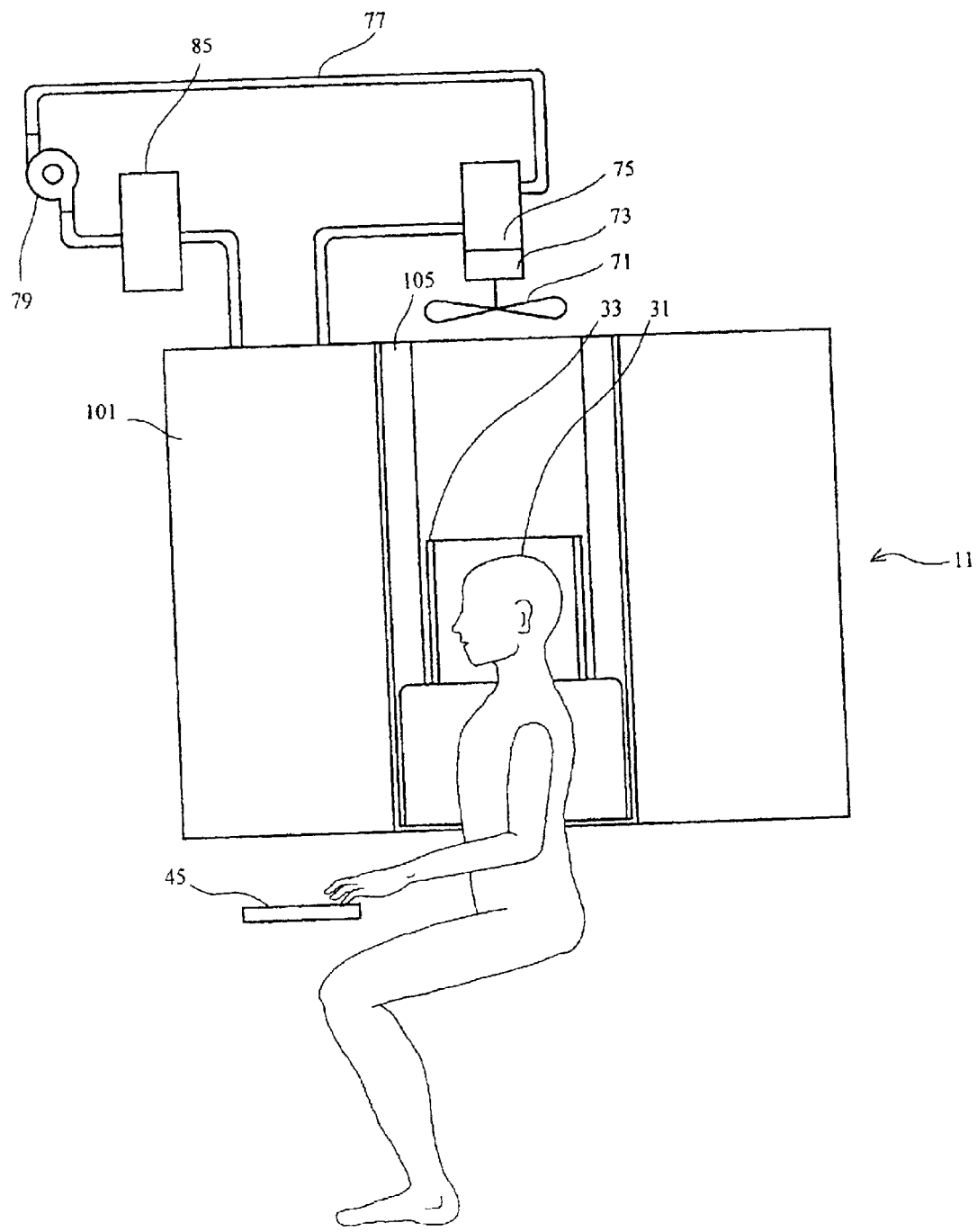
FIG. 8 shows an embodiment of the interrelation of the magnet system, the means for air feed, and the imaging subject during the imaging operation.

The air flow rate adjustment may also be performed by adjusting the flow rate supplied to the pipe passage 83 and flow rate supplied to the fluid motor 75 by means of the flow rate adjuster valve 81 installed in the pipe passage 83 bypassing the fluid motor 75 as shown in FIG. 7. The flow rate adjuster valve 81 is an example of the embodiment of the means for adjustment.

When the main magnetic field coil unit of the magnet system 11 is constituted of an ordinary conductive coil, the cooling of the ordinary conductive coil is performed by fluid to suppress the rise in temperature due to heat emitted by the ordinary conductive coil. Even if a superconductive coil is used, cooling by fluid is likely to be performed, when suppressing a rise in temperature is necessary in the gradient coil unit. When the magnet system 11 has such a liquid cooling device, the flow movement of the cooling liquid may also be utilized to turn the fluid motor 75.

In other words, when the interior of the magnet system 11 has a section for cooling such as a gradient coil unit or main magnetic field coil unit cooled by fluid made to circulate by a pump 79 while heat is emitted by the radiator 85, then the fluid motor 75 is installed in the flow path of the circulating fluid. Such an arrangement allows simplifying the structure by integrating the cooling system and the fluid motor drive system.

In such a structure, the air flow rate is appropriately adjusted by turning the clutch on and off and shifting the gears in the gear box 73. So there is therefore no change in the flow rate of the fluid even if the air flow rate is adjusted, and the air flow rate can be adjusted without affecting the cooling performance.

Figure 9:
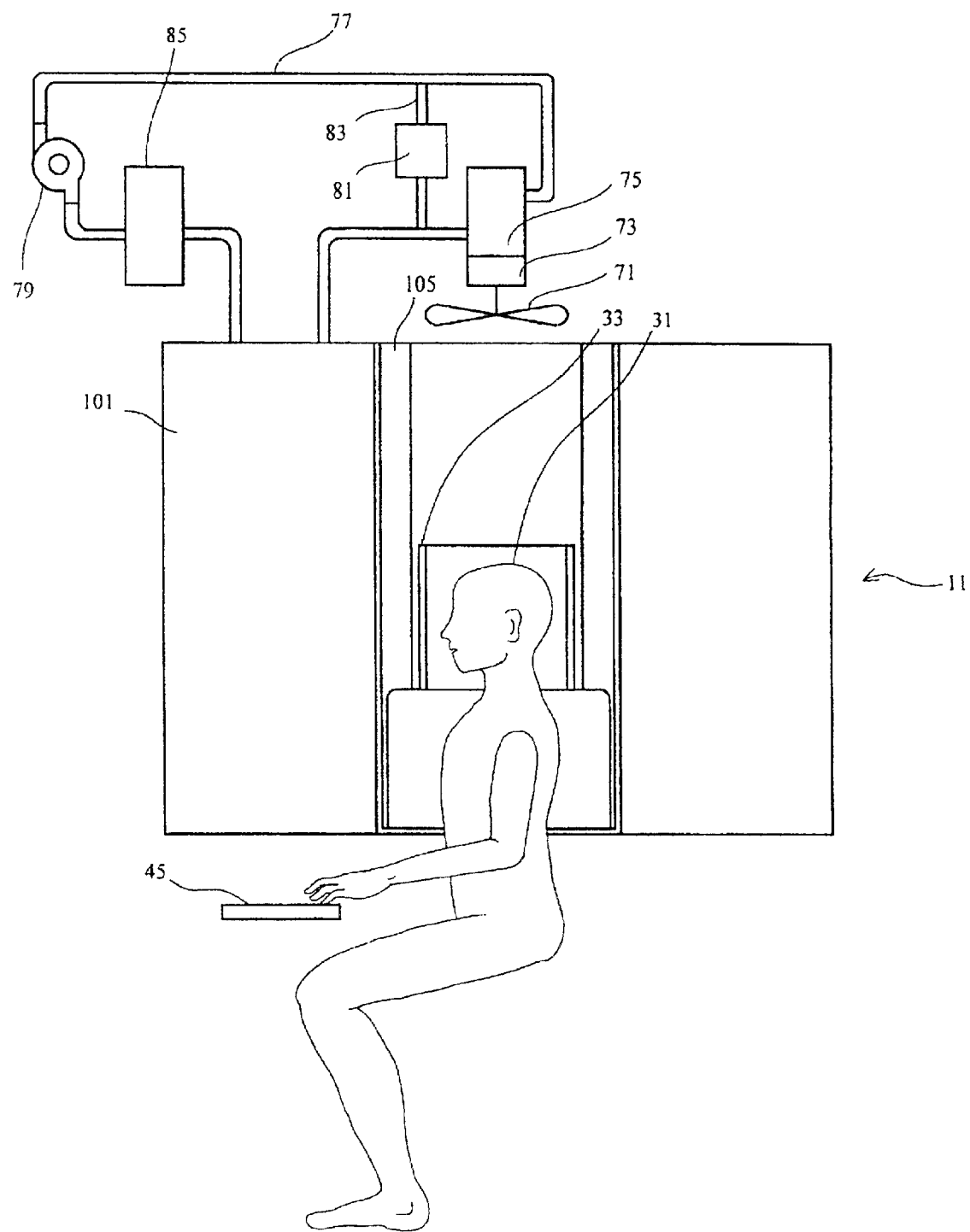
FIG. 9 shows an embodiment of the interrelation of the magnet system, the means for air feed, and the imaging subject during the imaging operation.

Alternatively, the air flow rate can be adjusted to an appropriate figure as shown in FIG. 9, by adjusting the ratio of the fluid flow flowing in the fluid motor 75 to the fluid flowing in the pipe passage 83 by means of the fluid motor 75 in the cooling fluid circulation path, the pipe passage 83 bypassing the fluid motor 75, and the flow rate adjuster valve 81 installed in the pipe passage 83. The overall flow rate quantity does not change even if this fluid flow ratio is adjusted, so the air flow rate can be adjusted without affecting the cooling performance.

The operation of the disclosed embodiments is as follows. The operator 35 first of all, seats the subject 31 in the seat 43 lowered inside the pit 21, so the head of the subject 31 is within the RF coil 33. The operator 35 next operates the switch 47 to operate the seat up/down mechanism 41, and raise the seat 43 to the imaging position shown in FIG. 5.

In this state, the fluid motor 75 operates, sending air (breeze) to the inner space of the magnet system 11. This air blow is performed intermittently while the subject 31 is present in the inner space. The subject 31 can therefore feel a pleasant cooling sensation even within the narrow inner space.

Figure 10:
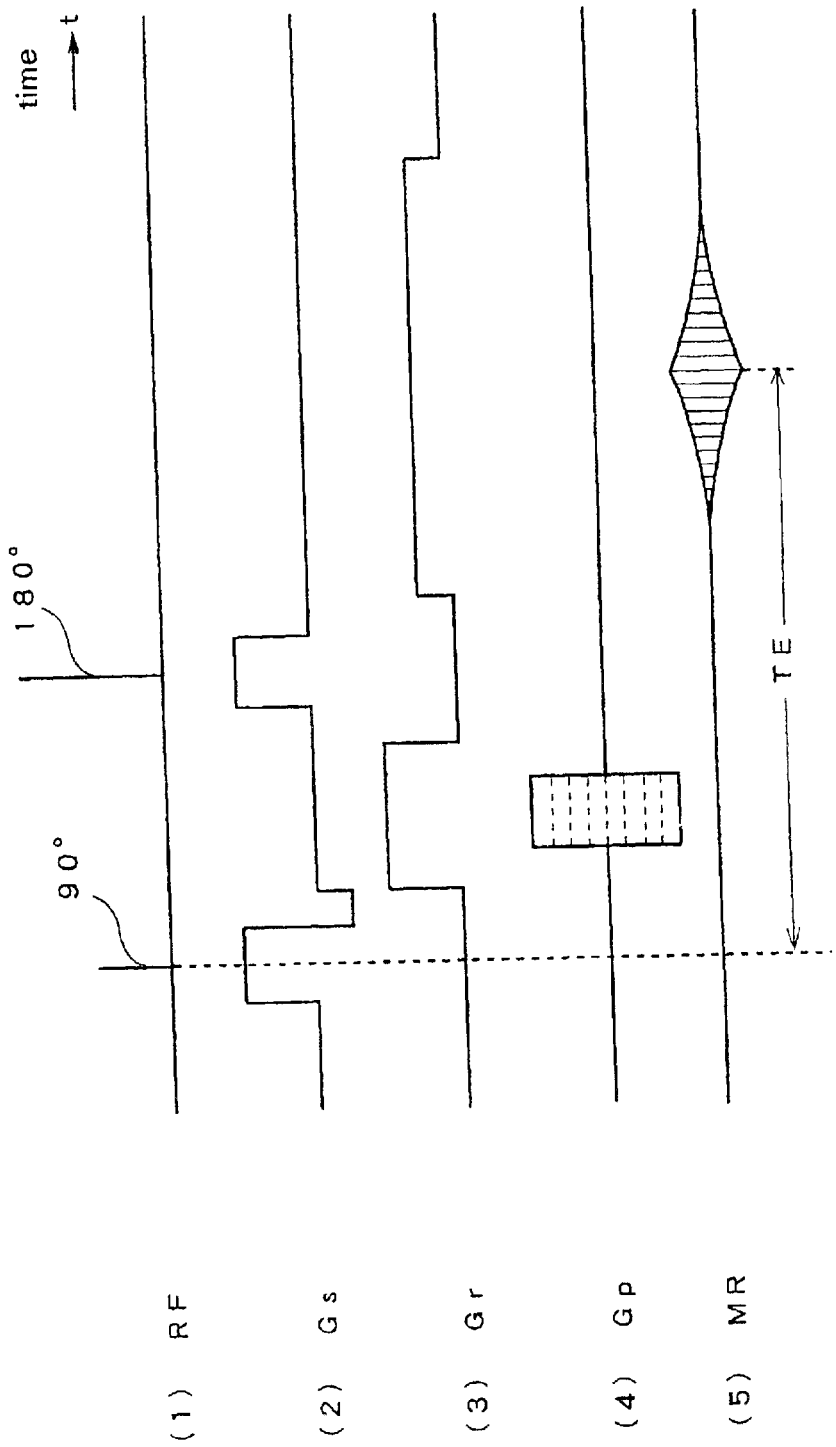
FIG. 10 shows an embodiment of a typical pulse sequence implemented by the system shown in FIG. 1.

The operator 35 next operates the operating unit 191 to start the imaging. The imaging proceeds under the control of the control unit 161. A typical pulse sequence utilized in the magnetic resonance imaging is shown in FIG. 10. This pulse sequence is an SE pulse sequence produced by the spin echo method.

In other words, (1) is an RF excitation 90 degree pulse and 180 degree pulse sequence by the SE method. In the same way, (2), (3), and (4) are respectively the slice gradient Gs, the readout gradient Gr, the phase encode gradient Gp and the spin echo MR sequences. The 90 degree pulse and 180 degree pulse respectively represent the center signals. The pulse sequence proceeds from left to right along the time axis t.

The 90 degree spin excitation is performed by the 90 degree pulse as shown in the same figure. The excitation selected for the specified slice applied with the slice gradient Gs is performed at this time. After 90 degree excitation at the specified time, 180 degree excitation by the 180 degree pulse or in other words, an inverted spin is performed. The slice gradient GS is also applied at this time, and selective inversion of the same slice is performed.

As shown in the same figure, the readout gradient Gr and the phase encode gradient Gp are applied in the period of 90 degree excitation and spin inversion. Spin dephasing is performed by the readout gradient Gr. Spin phase encoding is performed by the phase encode gradient Gp.

The control unit 161 controls the shifting of gears and turning of a clutch on and off. Needless to say, this control may be performed manually. The gear box 73 may be omitted when there is no need to adjust the rotational speed of the rotating vanes 71.

Figure 11:
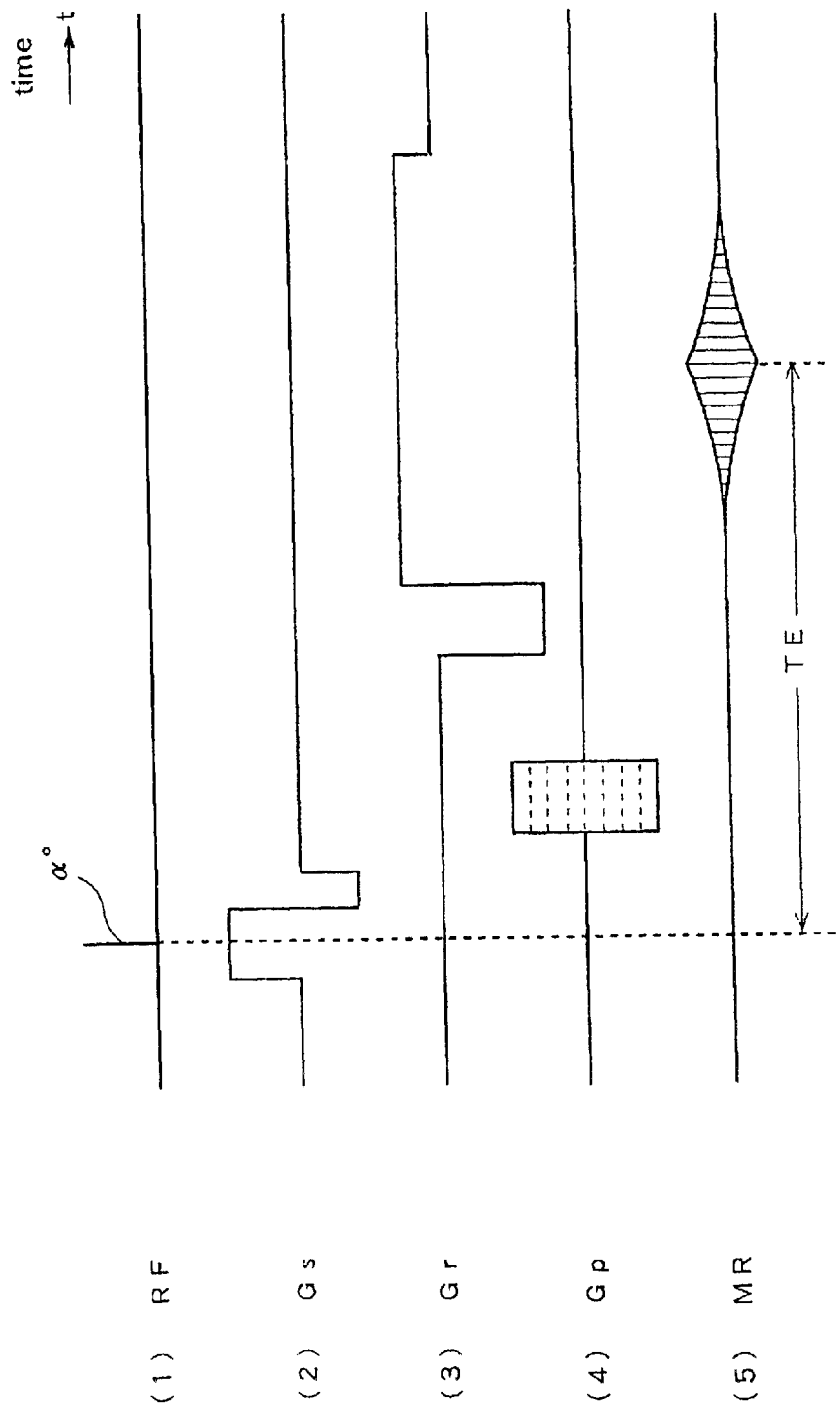
FIG. 11 shows an embodiment of a typical pulse sequence implemented by the system shown in FIG. 1.

Another magnetic resonance imaging pulse sequence is shown in FIG. 11. This pulse sequence is a GRE (gradient echo pulse) produced by the gradient echo method.

In other words, in the figure, (1) is the RF excitation $\alpha°$ pulse sequence in the GRE method. Also, (2), (3) and (4) are respectively, the slice gradient Gs, the readout gradient Gr, the phase encode gradient Gp and the gradient echo MR sequences. The $\alpha°$ pulse represents the center signal. The pulse sequence proceeds from left to right along the time axis t.

The spin $\alpha°$ excitation by the $\alpha°$ pulse is therefore performed as shown in FIG. 11. Here, $\alpha°$ is less than 90 degrees. The excitation selected for the specified slice applied with the slice gradient Gs is performed at this time.

After $\alpha°$ excitation, spin phase decoding is performed by the phase encode gradient Gp. Next, the spin is first dephased by the readout gradient Gr, the spin then rephased, and a gradient echo MR generated. The gradient echo MR is an RF signal having a waveform symmetrical with the echo center the center occurs at a point in time after echo time TE from the $\alpha°$ excitation.

The gradient echo MR is collected as view data by the data acquisition unit 151. A pulse sequence of this kind is repeated 64 to 512 times at a period TR (repetition time). The phase encode gradient Gp is changed each time the pulse sequence is repeated, and different phase encoding is performed each time. View data for views 64 to 512 are obtained in this way.

The view data acquired by means of the pulse sequences of FIG. 10 or FIG. 11 are collected in the memory of the data processing unit 171. The pulse sequence utilized in the imaging is not limited to the GRE method or the SE method and other methods such as FSE (Fast Spin Echo), and EPI (Echo Planar Imaging) may also be utilized as needed.

The data processing unit 171 performs two-dimensional inverse Fourier transforming of the view data and reconstructs a stepped image of the head of the subject 31. The reconstructed image is displayed as a viewable image on the display unit 181.

The brain functions of the subject 31 are examined based on the images acquired by imaging of the subject 31 while carrying out a specified keyboard operation. The keyboard operation is performed while the subject 31 is in an upright position so that the device is operated while the subject 31 is in the same state as a normally active human being. The imaging of brain functions can therefore be correctly performed while the subject 31 is in a normal active state.

Besides imaging the subject 31 while performing a task with his hands, imaging can be performed of the state of the brain for instance while the subject 31 is speaking a word, singing or remembering a thought, and the brain functions during routine activities can be correctly imaged. Imaging of brain behavior when sensory functions such as hearing, taste, smell, or feel are being stimulated can also be performed in the same way.

The example of a magnet system described above is for a vertical bore magnet system, however this invention is not limited to a vertical bore magnet system and a magnetic resonance imaging device utilizing a horizontal bore magnet system with the bore facing horizontally may also be installed in an air feed device as described above.

Examples of the structure of the magnet system section in a magnetic resonance imaging device of this kind are respectively shown in FIG. 12, FIG. 13, FIG. 14, FIG. 15 and FIG. 16. Of the figures, those sections the same as shown in FIG. 5, FIG. 6, FIG. 7, FIG. 8 and FIG. 9 have the same reference numerals so an explanation is omitted here.

Figure 12:
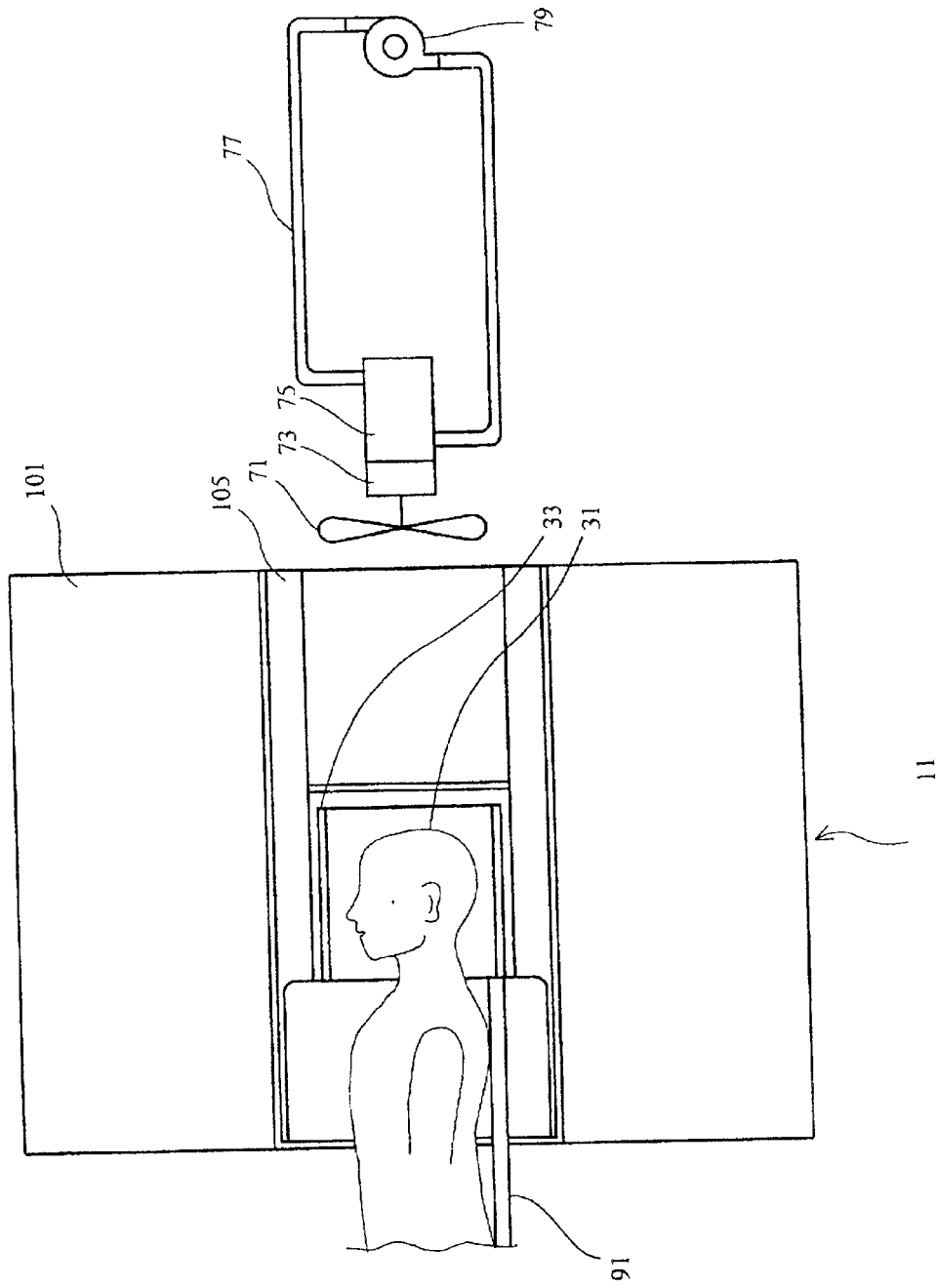
FIG. 12 shows an embodiment of the interrelation of the horizontal bore magnet system, the means for air feed, and the imaging subject during the imaging operation.
Figure 13:
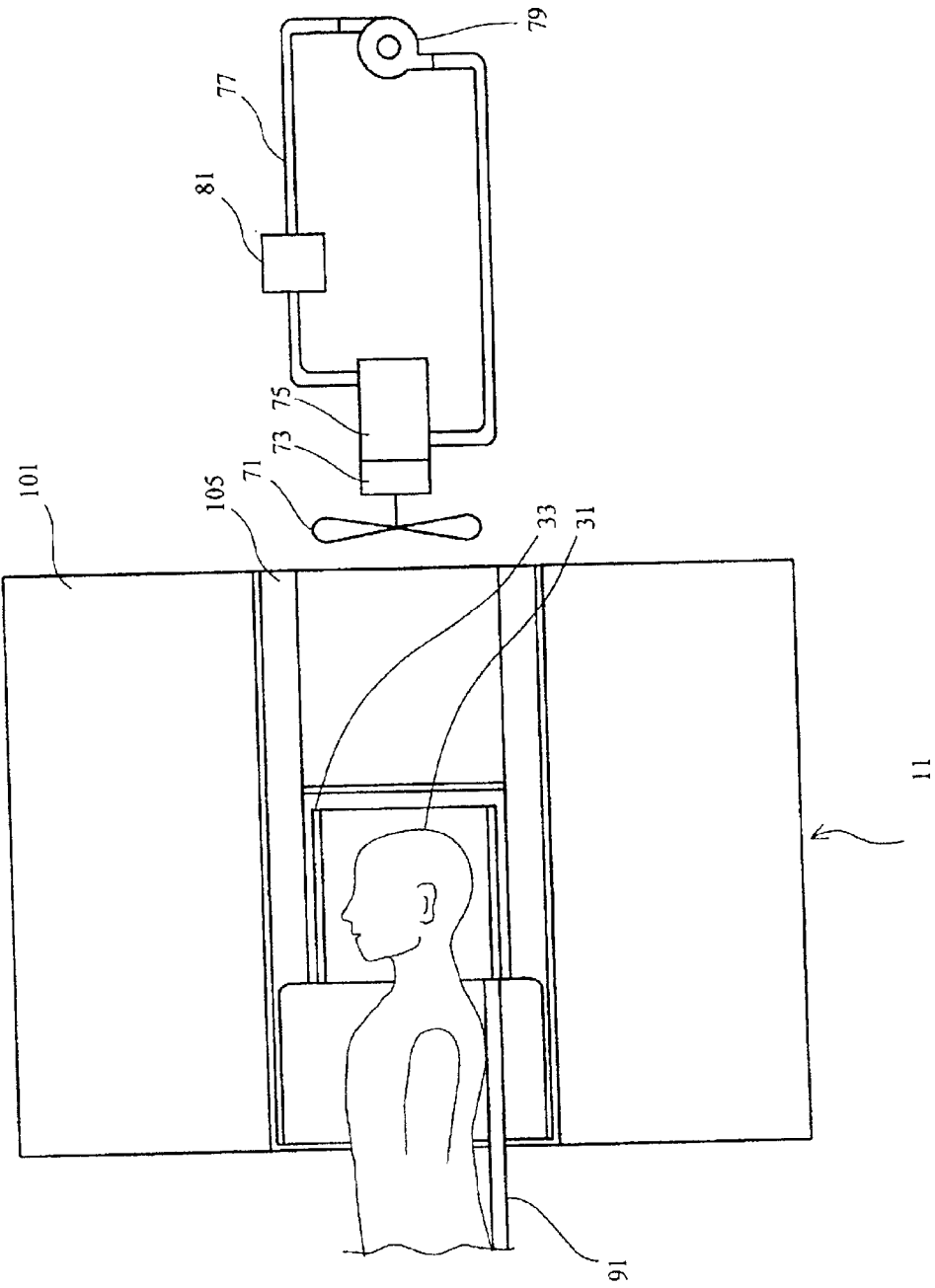
FIG. 13 shows an embodiment of the interrelation of the horizontal bore magnet system, the means for air feed, and the imaging subject during the imaging operation.
Figure 14:
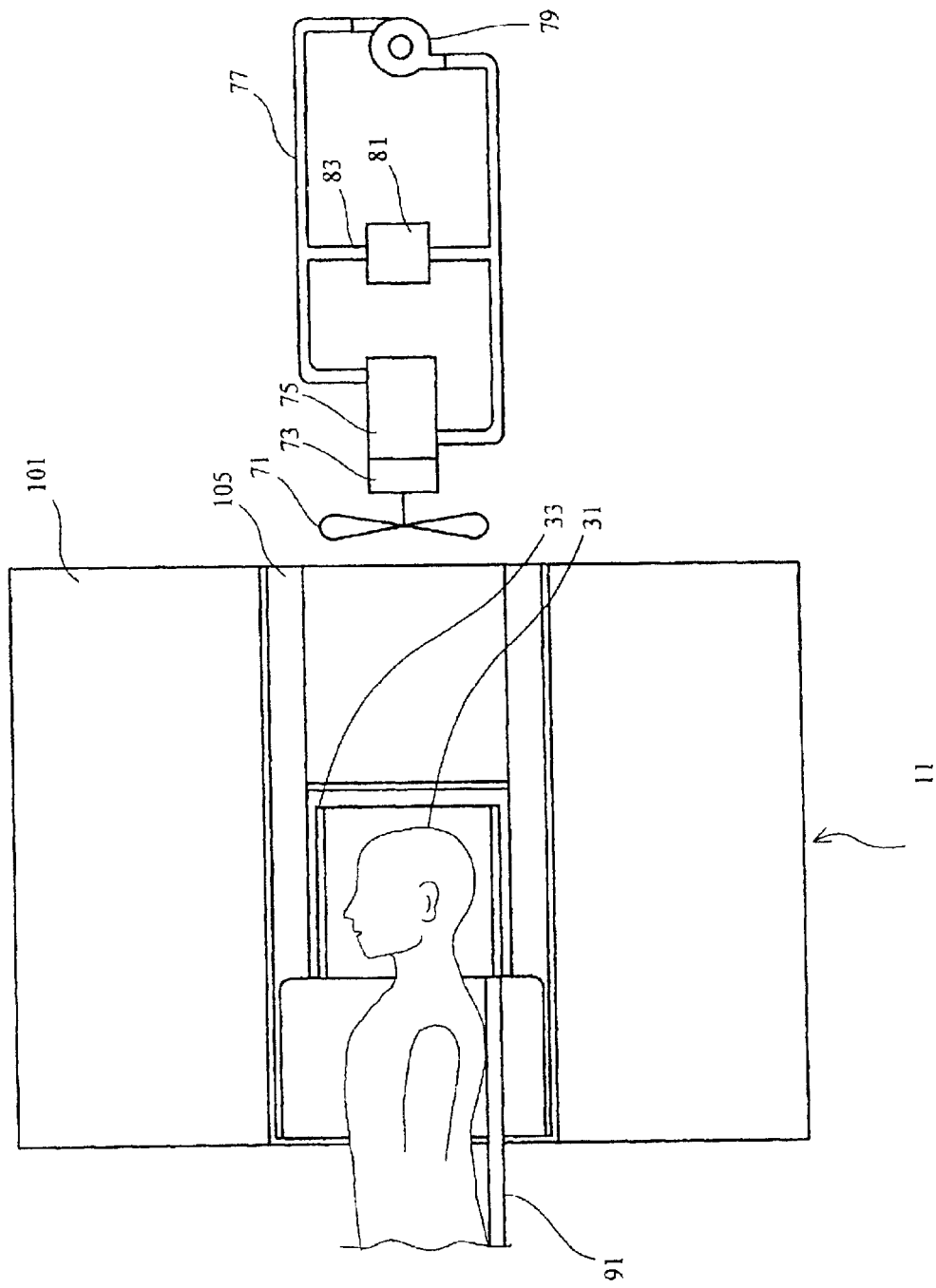
FIG. 14 shows an embodiment of the interrelation of the horizontal bore magnet system, the means for air feed, and the imaging subject during the imaging operation.
Figure 15:
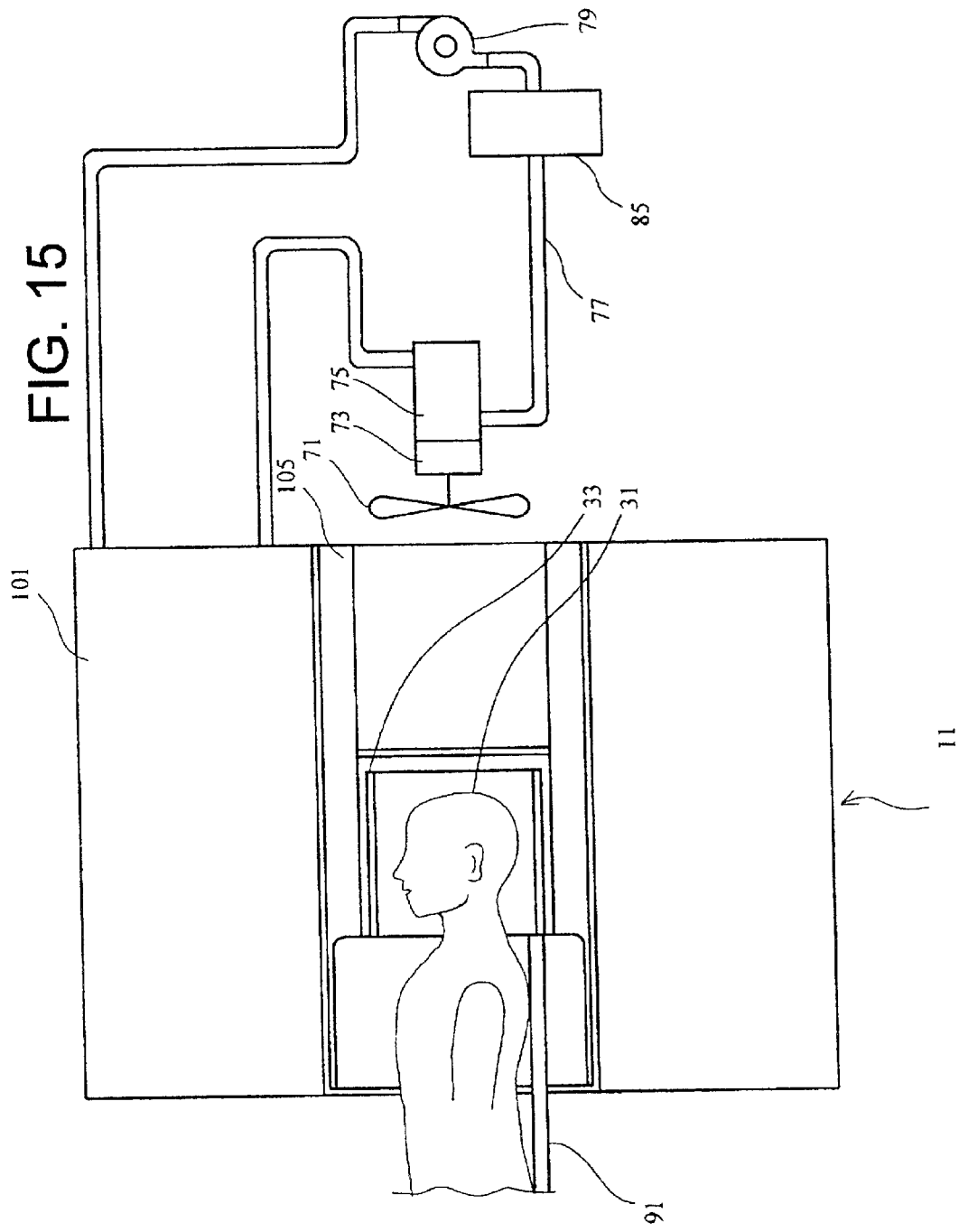
FIG. 15 shows an embodiment of the interrelation of the horizontal bore magnet system, the means air feed, and the imaging subject during the imaging operation.
Figure 16:
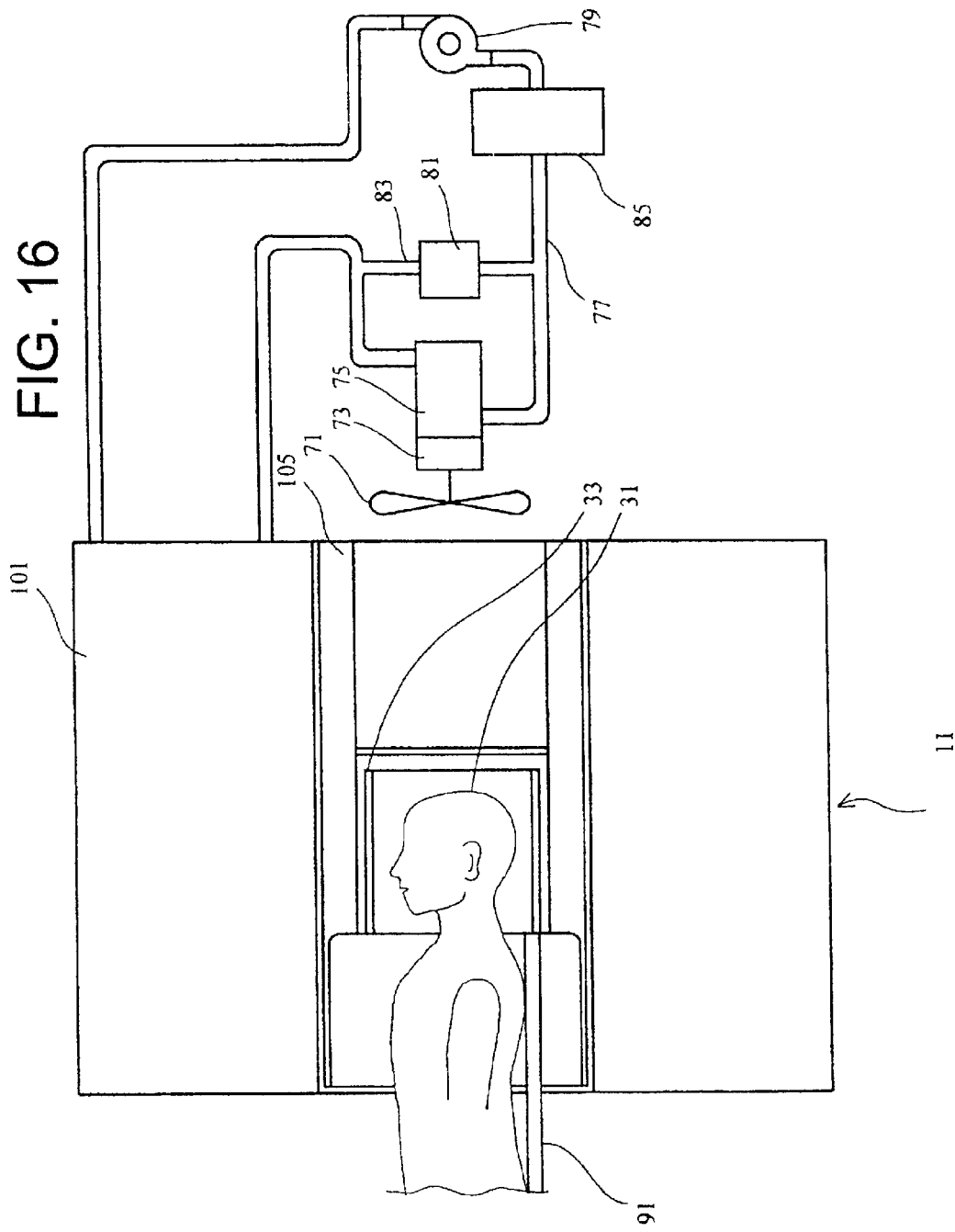
FIG. 16 shows an embodiment of the interrelation of the horizontal bore magnet system, the means for air feed, and the imaging subject during the imaging operation.

FIG. 12 shows a horizontal bore magnet system installed with means for air feed the same as shown in FIG. 5. In the same way, the horizontal bore magnet systems of FIG. 13, FIG. 14, FIG. 15 and FIG. 16 are respectively installed with means for air feed the same as shown in FIG. 6, FIG. 7, FIG. 8 and FIG. 9.

The inner space of the magnet system 11 as shown in these figures, is a columnar inner space having a horizontal center axis. The subject 31 is carried in and carried out of the inner space of the magnet system 11 mounted on a support plate 91. The RF coil 33 is attached to the support plate 91. Air is fed into this inner space by rotation of the rotating vanes 71 by means of the fluid motor 75.

The above imaging device was described for this invention with a magnetic resonance imaging device however the imaging device of this invention is not limited to use in a magnetic resonance imaging device and may utilize a signal acquisition device having a space to hold the imaging subject such as PET (positron emission tomography, gamma cameras (γ camera), X-ray CT(computed tomography) and other types of imaging devices may also be utilized.

Many widely different embodiments of the invention may be configured without departing from the spirit and the scope of the present invention. It should be understood that the present invention is not limited to the specific embodiments described in the specification, except as defined in the appended claims.

Various modifications in structure and/or steps and/or function may be made by one skilled in the art without departing from the scope and extent of the invention as recited in the claims.

What is claimed is:

1. A magnetic resonance imaging device comprising:
   means for signal acquisition that acquires a magnetic resonance signal;
   a space accommodating a subject for imaging;
   a fluid motor rotating by fluid flow and disposed adjacent to the space; and rotating vanes driven by the fluid motor and forcing air into the space, wherein the fluid motor and the rotating vanes do not cause electrical interference with the device.

2. The device of claim 1 comprising:

means for adjustment for adjusting fluid flow quantity supplied to the fluid motor.

3. The device of claim 1 comprising:

means for adjustment for adjusting ratio of fluid flow quantity supplied to the fluid motor to fluid flow quantity bypassing the fluid motor.

4. The device of claim 1 wherein the means for signal acquisition has a section to be cooled by fluid, and the fluid motor is driven by fluid to cool the section.

5. The device according to claim 1 wherein the rotating vanes are disposed above the subject.

6. The device according to claim 1 comprising:

means for supporting the subject in the space; and means for adjusting a position of the means for support.

7. The device according to claim 1 comprising:

means for positioning the subject in the space in a substantially vertical position.

8. The device according to claim 1 comprising:

means for positioning the subject in the space in a substantially horizontal position.

9. The device according to claim 7 wherein the rotating vanes are aligned substantially vertically with the subject.

10. The device according to claim 7 wherein the rotating vanes are aligned substantially horizontally with the subject.

11. A magnetic resonance imaging system comprising:

a magnet system having a space for positioning a subject therein;

means for acquiring a magnetic resonance signal;

means for providing a free flow of air into the space containing the positioned subject, the means being made from a non-magnetic or non metallic material that avoids interference with the magnet system or the means for acquiring a magnetic resonance signal, the means for providing a free flow of air being disposed externally of the magnet system and applied externally to the subject; and means for adjusting the position of the subject in the magnet system.

12. The system according to claim 11 wherein the means for providing a flow of air comprises:

rotating vanes; and means for rotating the vanes by fluid flow.

13. The system according to claim 12 wherein the magnet system has a vertical bore.

14. The system according to claim 12 wherein the magnet system has a horizontal bore.

15. The system according to claim 12 wherein rotating vanes are adjacent to one end of the magnet system.

16. A magnetic resonance imaging system comprising:

a magnet system having a space for positioning a subject therein;

means for acquiring a magnetic resonance signal;

means for providing a free flow of circulating air into the space containing the positioned subject, the means being made from a non-magnetic or non metallic material that avoids interference with the magnet system or the means for acquiring a magnetic resonance signal, the means for providing free circulating air flow being disposed externally to, and over the surface of, the subject at a temperature to cool the subject; and means for adjusting the position on the subject in the magnet system.

* * * * *